(12) United States Patent
Kyriakou et al.

(10) Patent No.: US 9,036,780 B2
(45) Date of Patent: May 19, 2015

(54) METHOD FOR RECORDING A FOUR-DIMENSIONAL ANGIOGRAPHY DATA RECORD

(71) Applicants: Yiannis Kyriakou, Spardorf (DE); Christoph Köhler, Forchheim (DE)

(72) Inventors: Yiannis Kyriakou, Spardorf (DE); Christoph Köhler, Forchheim (DE)

(73) Assignee: SIEMENS AKTIENGESELLSCHAFT, München (DE)

( * ) Notice: Subject to any disclaimer, the term of this patent is extended or adjusted under 35 U.S.C. 154(b) by 119 days.

(21) Appl. No.: 13/860,573

(22) Filed: Apr. 11, 2013

(65) Prior Publication Data

US 2013/0336450 A1    Dec. 19, 2013

Related U.S. Application Data

(60) Provisional application No. 61/623,096, filed on Apr. 12, 2012.

(30) Foreign Application Priority Data

Apr. 12, 2012 (DE) .................. 10 2012 205 935

(51) Int. Cl.
| | | |
|---|---|---|
| A61B 6/00 | (2006.01) | |
| A61B 5/00 | (2006.01) | |
| A61B 6/12 | (2006.01) | |
| A61B 5/0402 | (2006.01) | |
| A61N 1/05 | (2006.01) | |
| A61N 1/362 | (2006.01) | |
| G01R 33/48 | (2006.01) | |

(52) U.S. Cl.
CPC .............. *A61B 6/504* (2013.01); *A61B 5/0402* (2013.01); *A61B 5/7289* (2013.01); *A61B 6/12* (2013.01); *A61B 6/4441* (2013.01); *A61B 6/466* (2013.01); *A61B 6/481* (2013.01); *A61B 6/486* (2013.01); *A61B 6/503* (2013.01); *A61B 6/5241* (2013.01);

(Continued)

(58) Field of Classification Search
CPC .... A61B 6/504; A61B 5/0402; A61B 5/7289; A61B 6/12; A61B 6/4441; A61B 6/466; A61B 6/481; A61B 6/503; A61B 6/5241; A61B 6/0306; A61N 1/056; A61N 1/362; G01R 33/4812
USPC ................. 378/4, 8, 19, 62; 382/131, 128
See application file for complete search history.

(56) References Cited

U.S. PATENT DOCUMENTS

| | | | |
|---|---|---|---|
| 2006/0159326 A1* | 7/2006 | Rasche et al. | 382/131 |
| 2006/0285632 A1* | 12/2006 | Boese et al. | 378/8 |

(Continued)

FOREIGN PATENT DOCUMENTS

| | | |
|---|---|---|
| DE | 102006042997 A1 | 4/2008 |
| DE | 102006045423 A1 | 4/2008 |

(Continued)

*Primary Examiner* — Irakli Kiknadze

(57) ABSTRACT

A method for recording a four-dimensional angiography data record using an x-ray facility with a C-arm is proposed. Projection images are recorded from different projection directions at different time points of the cardiac cycle. A number of three-dimensional reconstruction image data records assigned respectively to a time segment of the cardiac cycle are reconstructed from the projection images and combined to form the four-dimensional angiography data record by temporal assignment in respect of the cardiac cycle. At least one recording parameter describing the temporal sequence is selected when recording the projection images as a function of cardiac stimulation performed to ensure a stable heart rate during recording so that the recording of the projection images takes place in such a manner that it is synchronized with the cardiac cycle.

15 Claims, 4 Drawing Sheets

(52) U.S. Cl.
CPC ............. *A61B 6/5264* (2013.01); *A61B 6/5288* (2013.01); *A61B 6/5294* (2013.01); *A61B 6/541* (2013.01); *A61N 1/056* (2013.01); *A61N 1/362* (2013.01); *G01R 33/4812* (2013.01)

(56) References Cited

U.S. PATENT DOCUMENTS

2010/0014629 A1* 1/2010 Boese ................................ 378/8
2010/0014726 A1* 1/2010 Schaefer et al. ............. 382/128
2011/0298793 A1* 12/2011 Lauritsch et al. ............. 345/419
2012/0087563 A1* 4/2012 Ionasec et al. ................ 382/131

FOREIGN PATENT DOCUMENTS

DE 102008016892 A1 10/2009
DE 102008052685 A1 5/2010

* cited by examiner

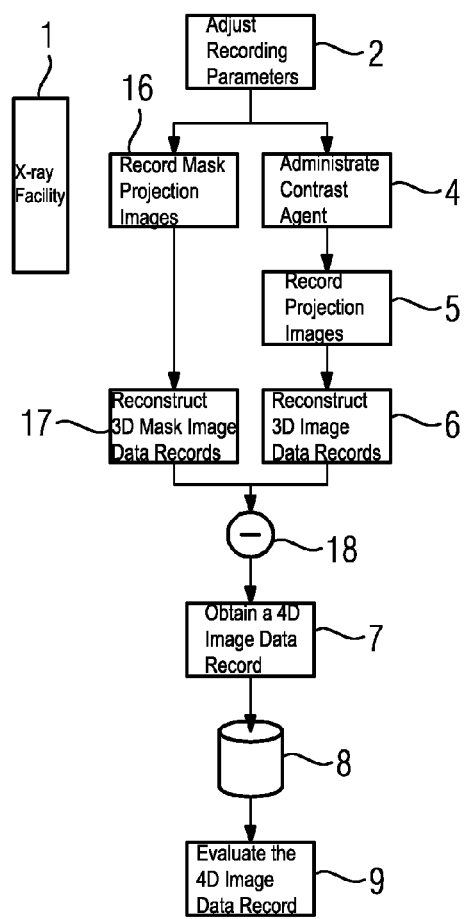
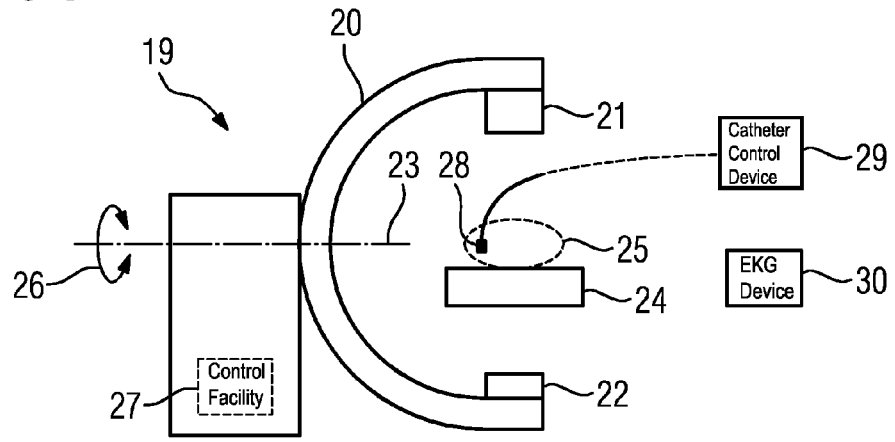

METHOD FOR RECORDING A FOUR-DIMENSIONAL ANGIOGRAPHY DATA RECORD

CROSS REFERENCE TO RELATED APPLICATIONS

The present application claims the benefit of a provisional patent application filed on Apr. 12, 2012, and assigned application No. 61/623,096. The present application also claims the benefit of a German application No. 10 2012 205 935.0 filed Apr. 12, 2012. Both of the applications are incorporated by reference herein in their entirety.

FIELD OF INVENTION

The invention relates to a method for recording a four-dimensional angiography data record using an x-ray facility with a C-arm, wherein projection images are recorded from different projection directions at different time points of the cardiac cycle, a number of three-dimensional reconstruction image data records assigned to a time segment of the cardiac cycle are reconstructed from the projection images and combined to form the four-dimensional angiography data record by temporal assignment in respect of the cardiac cycle. The invention also relates to an x-ray facility with a C-arm.

BACKGROUND OF INVENTION

In the prior art digital subtraction angiography, abbreviated to DSA, is already a widely known image recording method for recording images of a vascular system of a patient with high quality, showing the vessels clearly. On the one hand images of the vascular system are recorded, with a contrast agent having been administered to the patient beforehand, so that the contrast agent-filled vessels can be identified particularly clearly on said images. When mask images, which were recorded before the contrast agent was present in the vascular system to be recorded without moving the patient, are subtracted from these contrast agent images (frequently also referred to as fill images), apart from noise effects only the signal components of the contrast agent remain, so that an excellent assessment of the resulting DSA images is possible.

DSA is not only used in instances where the vascular structure of a patient is essentially mapped or assessed but for moving images, in other words for example when the movement of the heart is to be observed. Time-based two-dimensional digital subtraction angiography is primarily known here, in which in the fill phase, in other words when the contrast agent is essentially evenly distributed in the vascular system being examined, two-dimensional fluoroscopy images of the patient are recorded repeatedly, from which for example mask images can be subtracted according to the cardiac phase. However it has also been proposed that a four-dimensional angiography data record should also be created when recording the vascular system in the region of the heart, to show the movement of the heart and the surrounding vessels over an entire cardiac cycle, in other words a three-dimensional volume moving over a cardiac cycle. Angiography data records showing this are referred to as four-dimensional angiography data records, as they show a temporal profile of a three-dimensional volume.

To record such four-dimensional angiography data records, it has been proposed, when an x-ray facility with a C-arm is used, for example in an angiography laboratory, that projection images should be recorded from different projection directions at different time points of the cardiac cycle. If an electrocardiogram (EKG) is traced at the same time, the recorded projection images can be assigned to different phases or time segments of the cardiac cycle. In other words the cardiac cycle is broken down into different time segments, with the projection images recorded within a time segment being organized respectively into a set of projection images. Each of these sets of projection images is then used respectively to generate a three-dimensional reconstruction image data record assigned to the time segment. If these three-dimensional reconstruction image data records are then combined by temporal assignment in respect of the cardiac cycle, the four-dimensional angiography data record results. Ultimately the known procedure for x-ray facilities with a C-arm is a multisegment reconstruction based on a retrospective evaluation of the EKG signal, which was recorded at the same time as the projection images.

However this approach has disadvantages. Firstly it requires a number of rotations of the C-arm. This is because the irregularity of the heart movement means that the projection images of a time segment are not necessarily evenly distributed over the covered projection directions. An attempt is therefore made to achieve the broadest possible data base, which allows halfway even coverage of the projection angle interval to be recorded for all time segments. However this is not always possible because of the unpredictability of the heart movement. This unpredictable heart movement during the different cardiac cycles is also the reason why the retrospective evaluation of the EKG signal is not always useful in practice. It should in particular be noted here that the acquisition time is generally very long, for example 20-30 seconds. There is a high level of radiation exposure and the timing in respect of the contrast agent bolus is extremely complex, particularly when a number of C-arm runs are required and contrast agent may even have to be administered more than once.

SUMMARY OF INVENTION

The object of the invention is therefore to specify a method for recording a four-dimensional angiography data record, with which it is possible to reconstruct the recorded vascular system for different time segments of the cardiac cycle as completely as possible and with high quality.

To achieve this object, provision is inventively made with a method of the type mentioned in the introduction for at least one recording parameter describing the temporal sequence to be selected when recording the projection images as a function of cardiac stimulation performed to ensure a stable heart rate during recording, so that the recording of the projection images takes place in such a manner that it is synchronized with the cardiac cycle.

The invention therefore uses a predictability of the heartbeat in a specified time period to match the recording of the projection images exactly to the heartbeat. In other words it is possible by selecting in particular the recording time and/or the movement of the C-arm appropriately to synchronize the timing of the recording of the projection images using the C-arm with the cardiac cycle so that the projection images for each time segment of the cardiac cycle are recorded with even distribution in respect of the projection directions. This allows complete reconstruction with the fewest artifacts possible for the individual time segments, allowing a particularly high quality four-dimensional angiography data record to be generated.

Heart stimulation that ensures a stable heart rate during recording is frequently also referred to as "pacing". According to the invention so-called "slow cardiac pacing" is provided, with which the heart rate can be maximum 130 beats per minute (bpm), so that the significance of induced ventricular tachycardia is extremely small. This is in contrast to so-called "rapid cardiac pacing", with which "palpitations" are deliberately produced, for example when a minimally invasive intervention that has to be performed with extreme locational precision is undertaken at the heart or on an adjacent vessel. Using slow cardiac pacing makes heart movement reproducible and is the basis for cycle-synchronized recording of the x-ray projection images. Using slow cardiac pacing on the one hand ensures that "realistic" conditions are present, from which conclusions can be drawn about the non-stimulated operation of the heart but on the other hand the transportation of the contrast agent through the vascular system which is to be recorded and in particular includes the heart operates normally. Provision can expediently be made here for the heart rate to be set at 80 to 130 bpm, in particular 95-105 bpm. 100 bpm has proven particularly suitable.

Heart stimulation, which ensures a stable heart rate during recording, can be achieved for example by way of a so-called pacing catheter introduced into the patient, which can also be used in the context of minimally invasive interventions when heart movement is to be monitored. The inventive method is therefore particularly suitable in instances where a minimally invasive intervention is to take place, optionally also a diagnostic examination, in which there is a pacing catheter present in the heart of the patient anyway. This pacing catheter is now activated, so that the desired stable heart rate, for example 100 bpm, is present.

One of the ideas underlying the present invention is therefore first to generate a reliable, predictable heartbeat, so that the stable heart rate can only be achieved with improved timing of the recording of the projection images by corresponding adjustment of recording parameters. As already mentioned above, the setting of a heart rate that can be used for planning preferably takes place with corresponding activation of a pacing catheter in the heart of the patient, in particular by way of a corresponding catheter control device, which can be connected to a control facility that at least partially performs the inventive method.

Provision can expediently be made here for an EKG to be captured parallel to the projection images and the assignment of the projection images to a time segment to be checked as a function of their recording time and the EKG, but this is not absolutely necessary, as the inventively performed synchronization already allows a clear assignment of the projection images to different time segments of the cardiac cycle and this is also reliable due to the stable heart rate.

In one particularly advantageous embodiment of the present invention provision can be made for all the projection images to be recorded during a single rotational movement of the C-arm. The inventive perfect time matching therefore allows all the projection images required for the reconstruction of a four-dimensional angiography data record to be recorded within a single rotation, therefore with a reduced x-ray dose and where applicable with a reduced contrast agent dose.

Provision can further be made for the synchronization of the recording activity with the stable, predictable heart movement to be such that a projection image for each time segment of the cardiac cycle is recorded in each cardiac cycle, with the recording frequency of the projection images being selected as a multiple of the heart rate in particular. This allows the intended synchronization to be achieved in a particularly simple and complete manner, if a whole-number multiple of the stable heart rate is selected as the recording frequency for the recording arrangement of the C-arm, consisting of radiation source and radiation detector. The whole-number multiple here indicates how many images should be recorded per cardiac cycle and can correspond for example to the number of considered time segments of the cardiac cycle. It is however also conceivable to assign a number of images of a single cardiac cycle to the same time segment, whereby it may be expedient in this context still to record an EKG parallel to the recording of the projection images or to match the heart stimulation exactly, in order to be able to distinguish longer time segments of the cardiac cycle from shorter time segments of the cardiac cycle in a reliable manner.

The temporal synchronization or accordingly the recording parameters can be selected so that 30-40, in particular 35, projection images are recorded for each time segment. It has proven that, in particular with a precise temporal assignment, as permitted with the present invention, 30-40 images may be sufficient to generate reconstruction image data records of sufficiently high quality for the individual time segments, which can then be combined to form the four-dimensional angiography data record.

It is further advantageous, as mentioned above, for the projection images to be recorded during a fill phase after administration of a contrast agent. In particular the procedure which is coordinated temporally with the stable heart movement therefore allows contrast agent to be administered just once so that the projection images can be recorded during a single fill phase. As mentioned above, this limits the quantity of contrast agent that has to be administered and the corresponding exposure of the patient.

To determine when the fill phase, in which the contrast agent is essentially evenly distributed in the vascular system to be examined, in particular the heart and surrounding vessels, various options are conceivable within the context of the present invention, it being possible to use these as alternatives.

It is therefore possible in a first, less preferred embodiment of the present invention after administration of a test bolus for a series of two-dimensional images to be recorded, from which a delay time is determined, in particular automatically, after administration of the main bolus. Such test bolus measurements are known in principle with a smaller quantity of contrast agent being administered than for the main bolus, after which successive test bolus images are recorded, which show the initial distribution phase, the fill phase and the outflow phase, so that it can be concluded when the contrast agent main bolus has completely filled the vessels of the vascular system to be examined (and in particular also the heart). A sort of delay time after administration of the main bolus can then be calculated from this, at which the measurement can be started, in particular automatically.

According to the invention it is however preferred for fluoroscopy or 2D DSA monitoring to be performed before the recording of the projection images and after administration of the contrast agent, to monitor the spread of the contrast agent. The spread of the contrast agent bolus in the vascular system to be examined and/or in the heart is therefore constantly monitored, so that a user can start the recording of the projection images manually; it is however also conceivable for automatic monitoring to take place based on the recorded fluoroscopy images or 2D DSA monitoring images, particularly by observing the vein carrying the contrast agent out of the imaging region to be recorded. When it is full of the contrast agent, the measurement can also be started automatically. The two-dimensional fluoroscopy or 2D DSA images, which are recorded continuously or at short time intervals, are recorded with a low dose here, so that radiation exposure can be kept as low as possible for the patient.

It may also be particularly advantageously possible within the context of the present invention to operate digital subtraction angiography, by recording mask projection images subject to the same heart stimulation with the same recording parameters, from which three-dimensional mask image data records are determined for each time segment of the cardiac cycle, which are subtracted from the reconstruction image data records to determine the image data records on which the angiography data record is based. It is therefore also possible to record the mask images in a synchronized manner with the stable heart rate, so that three-dimensional mask image data records generated from the mask images are of a similarly good quality. Performing subtraction at the level of the three-dimensional image data records is advantageous in that it is no longer necessary to match the start of acquisition precisely to a specified cardiac phase or a specified time point in the cardiac cycle, as with a projection-based subtraction, which is in principle of course also conceivable, each of the projection images would have to be recorded at exactly the same time point or at least time segment in the cardiac cycle as the corresponding mask image to be subtracted. With a three-dimensional reconstruction this relationship is no longer relevant, as the mask projection images are distributed evenly over the covered projection angle interval and therefore mask image data records can be reconstructed, which are of the same high quality as the reconstruction image data records in respect of reconstruction. Of course the patient should not be moved between the recording of the mask projection images and the actual projection images, to ensure optimum correspondence.

According to the invention it is possible in principle to perform a known multisegment reconstruction based for example on the Feldkamp algorithm, which uses one of the projection images that is assigned exactly to the time segment being considered for each cardiac cycle completed during the recording of the projection images. This allows movement blurring to be largely avoided but generally very few images are used for the three-dimensional reconstruction, so for example sampling artifacts can occur. However alternative, particularly advantageous reconstruction systems are also conceivable in the context of the present invention, which extend the data base and improve the quality of the individual reconstruction image data records as a function of projection images not associated with the current time segment of the cardiac cycle. Thus for example provision can be made, for the reconstruction of the reconstruction data records, for projection images of adjacent time segments of the cardiac cycle to be taken into account with a lower weighting. Weighting systems are therefore possible, which can be provided differently for each time segment, depending on how significant the heart movement turns out to be in respect of the adjacent time segments. For example a triangular or trapezoidal weighting function can be applied, the breadth of which can be selected individually in particular for different time segments. However a fixed weighting of the directly adjacent projection images and optionally further, less directly adjacent projection images is also conceivable, so that ultimately in other words generally in this embodiment of the inventive method projection images of adjacent time segments are also included in the determination of the reconstruction image data record of a considered time segment with a lower weighting. This extends the data base and increases image quality. Noise and sampling artifacts are reduced. This is slightly at the expense of temporal resolution.

In one particularly advantageous embodiment of the present invention provision can however also be made for an iterative method to be used to determine the reconstruction image data records, in which a three-dimensional orientation image data record reconstructed from all the projection images is taken into consideration during the reconstruction of the reconstruction image data records. With such iterative reconstruction methods known in principle in the prior art a reconstructed volume, which was calculated using all the projection images (mean image without temporal resolution) is combined with the individually reconstructed individual volumes of the individual time segments, so that a further reduction of noise and sampling artifacts results. Reference should be made here for example to the McKinnon-Bates algorithm.

In a further embodiment of the present invention provision can also be made for the reconstruction image data records to be corrected in respect of instruments disposed within the patient to be recorded, in particular catheters, in particular by applying metal artifact reduction algorithms. The reconstruction image data records of the individual time segments can therefore be treated with known algorithms, for example based on interpolation, for reducing metal artifacts to avoid catheter artifacts. If the inventive method is used against a background, in which for example the contrast agent is administered by way of a catheter, in particular a so-called pigtail catheter, and/or a pacing catheter for heart stimulation is also recorded, such algorithms, which are generally used in respect of metal artifacts, are very useful in order to achieve a greater improvement in image quality. Of course the correction algorithms can also be applied to optionally further, different instruments within the body, for example a treatment catheter.

The inventive method delivers a high quality four-dimensional angiography data record, which can be used in many ways, in particular in respect of diagnostic tasks and/or monitoring/assistance during a minimally invasive intervention.

Provision can be made for example, as a basis for such further use of the four-dimensional angiography data record, for at least one vessel and/or organ, in particular the heart, to be segmented in the angiography data record and for the segmentation result to be used to derive a movement model of the segmented vessel and/or organ. In particular a movement vector field and/or the movement of each voxel over the entire cardiac cycle can be determined here. The four-dimensional reconstruction is therefore first used to deploy standard segmentation algorithms known in the prior art so that the positions of for example the heart wall and the heart lumen, vessels around the heart, the ventricles and the like can be determined respectively in the time segments. This segmentation of walls and lumen is now used to determine a movement model, for example a movement vector field, which shows the movement in particular of each segmented voxel over time.

This movement model can now be used for example to animate a static secondary image data record, which also shows the vessel and/or organ. This means that movements are impressed on an actually static image based on the movement derived from the four-dimensional angiography data record, for which purpose of course the secondary image data record is registered with the angiography data record, in particular a reconstruction image data record of the angiography data record of the time segment, in which the secondary image data record was recorded. It is possible thus to animate a high quality secondary image data record that is not four-dimensional, which was recorded before the intervention, it being possible to use for example a cardiac magnetic resonance image data record or a cardiac MSCT image data record as secondary image data records. In other words in this embodiment of the present invention the movement determined using the x-ray facility with the C-arm is used to transform the static data of the secondary image data record dynamically.

Such an animated secondary image data record can particularly advantageously be displayed when monitoring an intervention to be performed on the recorded patient as a function of a recorded EKG, being superimposed in particular with a current fluoroscopy image. The animated secondary image data record thus recorded can be registered for example on two-dimensional fluoroscopy images using methods that are known in principle. If a synchronization is then performed with the known and current EKG signal, which is recorded continuously, a phase-correlated superimposition of the secondary image data record onto the two-dimensional live fluoroscopy images can be achieved, which can then be used for navigation and guidance during in particular minimally invasive interventions, for example interventions at the heart. As the electrocardiogram that is actually present and was recorded in particular without cardiac pacing and the heart rate during the recording of the projection images can differ, assignment takes place based on the time segments, in other words relative phases of the cardiac cycle are used.

In a further embodiment of the present invention provision can particularly advantageously be made for at least one wall of at least one vessel and/or organ, in particular the heart, to be segmented in the angiography data record and for a movement model of the wall, in particular including a wall thickness that is a function of the time point in the cardiac cycle, to be determined. Such a movement model of the wall can then be displayed, to allow a diagnostic assessment. A display in the manner of an ultrasound image is conceivable here for example. The recorded movement, which can be taken from the four-dimensional angiography data record, can therefore be used for example to generate in particular ultrasound-type images, which show the movement of the wall, in particular the heart wall. The extent of the movement, as shown by the corresponding movement vector and its components, allows pathological tissue, for example infarction tissue, to be identified, so that the present invention is also advantageous in respect of a diagnosis still to be performed.

An x-ray facility with a C-arm, on which a radiation source and a radiation detector are disposed opposite one another, can therefore be embodied such within the context of the present invention that a control facility of the x-ray facility executes the inventive method. This means that the control facility receives the information relating to heart stimulation, in particular a set stable heart rate, and can activate the C-arm and/or recording arrangement accordingly, so that the two-dimensional projection images are recorded in a synchronized manner with the heartbeat. The further embodiments of the present invention described can also be achieved by way of such an x-ray facility.

BRIEF DESCRIPTION OF THE DRAWINGS

Further advantages and details of the present invention will emerge from the exemplary embodiments described in the following and with reference to the drawing, in which:

FIG. 5 shows a flow diagram of a second exemplary embodiment of the inventive method, and FIG. 6 shows an x-ray facility for performing the inventive method.

DETAILED DESCRIPTION OF INVENTION

Figure 1:
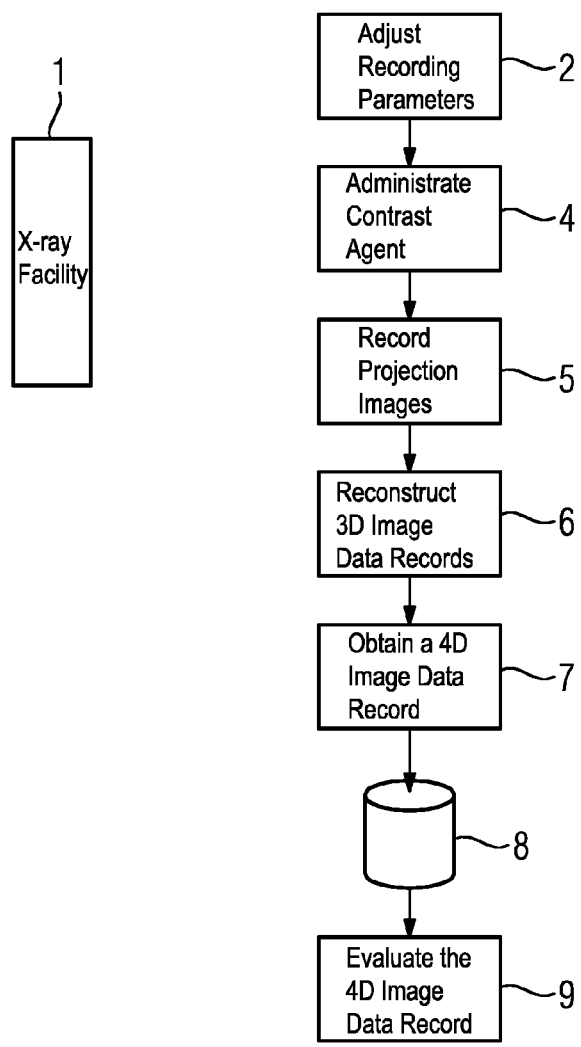
FIG. 1 shows a flow diagram of a first embodiment of the inventive method.

FIG. 1 shows a flow diagram of an exemplary embodiment of the inventive method for generating a four-dimensional angiography data record of the heart and its surroundings, containing movement information relating to an entire cardiac cycle.

The present invention here is based on heart stimulation present during the entire recording time for projection images using an x-ray facility with a C-arm, resulting in a stable heart rate, in the present exemplary embodiment 100 beats per minute (bpm). This is shown in FIG. 1 by the box 1. Such cardiac pacing can be achieved for example by way of a so-called pacing catheter, which has been inserted into the heart of the patient, by correspondingly activating said catheter, which can also be done for example by way of a control facility of the x-ray facility or is also conceivable by way of an external catheter control facility. In any case the information relating to the active heart stimulation and the associated heart rate is available to the control facility of the x-ray facility.

It is therefore possible in a step 2 to adjust the recording parameters of an upcoming acquisition of two-dimensional projection images from different projection directions to the known cardiac behavior during the acquisition time so that the recording of the two-dimensional projection images is synchronized with the externally predetermined heart movement, which can then be predicted. Provision is made here for selecting the recording frequency of the recording arrangement of the C-arm, consisting of the radiation source and radiation detector, so that it corresponds to a multiple of the heart rate. It is therefore decided in step 2 in the present exemplary embodiment, based on the heart rate used here of 100 beats per minute and the contrast agent bolus then present during recording, that all the projection images can be recorded during a single rotation of the C-arm and finally 35 projection images are available for each time segment of the cardiac cycle.

Figure 2:
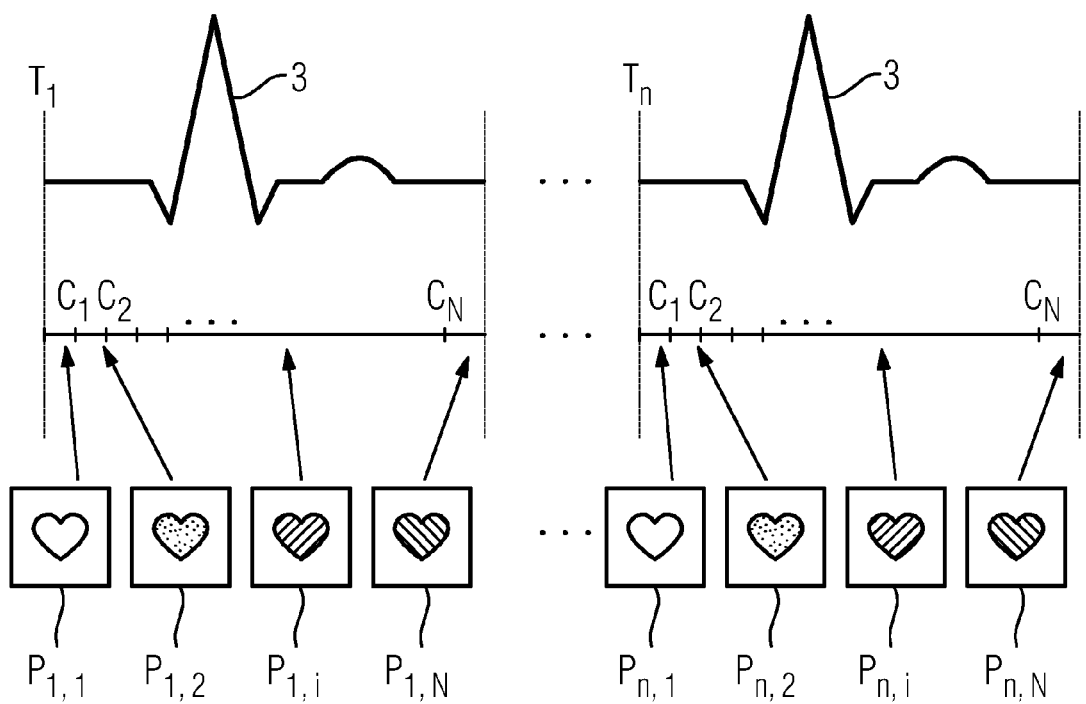
FIG. 2 shows a diagram of the inventively performed synchronization.

The synchronization of the recording activity with the cardiac activity is shown in more detail by FIG. 2. The profile 3 of an entire cardiac cycle is shown schematically there in the upper region starting at two time points $T_1$ and $T_n$. The cardiac cycle is now divided into N time segments $C_1, C_2, \ldots, C_N$. In the present instance all the time segments $C_1$ to $C_N$ are selected to be of equal size and the recording frequency of the projection images is set at N times the heart rate. This means however, as the heart rate is stable, that for each cardiac cycle j projection images $P_{j,1}$ to $P_{j,N}$ (starting at time point $T_j$) are recorded, one of which can be assigned respectively to one of the time segments $C_i$ with i=1, ..., N, as shown by the arrows in FIG. 2 for the projection images $P_{1,1}$, $P_{1,2}$, $P_{1,j}$, $P_{1,N}$, $P_{n,1}$, $P_{n,2}$, $P_{n,i}$, $P_{n,N}$ shown by way of example for the time points $T_1$ and $T_n$. The inventively performed synchronization of the recording operation with the actual cardiac behavior therefore results in an even distribution of the projection images $P_{j,i}$ assigned to the time segments $C_i$ over the covered projection angle interval.

However first in the exemplary embodiment illustrated in FIG. 1 after administration of the contrast agent two-dimensional fluoroscopy images are recorded continuously in a step 4, showing the initial distribution of the contrast agent in the heart region. It is also conceivable to determine and display 2D DSA images. It is now assessed, based on an automatic evaluation or by a user, whether the fill phase has been reached, in other words whether the contrast agent is essentially evenly distributed in the heart and the surrounding vessels of interest. If the fill phase has been reached, the actual recording of the projection images starts in a step 5 according to the synchronization system determined in step 2 and explained in FIG. 2, as described by recording parameters. It should however be noted here that it is also conceivable, instead of step 4, to perform a test bolus measurement, from which a delay time is then derived automatically and/or manually, with the recording in step 5 starting in particular automatically at the end of the delay time after administration of the contrast agent.

In step 5 the projection images are then recorded from different projection directions, it being possible to assign the projection images $P_{j,i}$ to their corresponding time segments $C_i$ based on the known heart stimulation and/or an EKG recorded in a parallel manner. Different sets of projection images are therefore ultimately available, which are all assigned to the same time segment, with the recording being performed in the present instance so that 35 projection images exist for each of the time segments.

Figure 3:
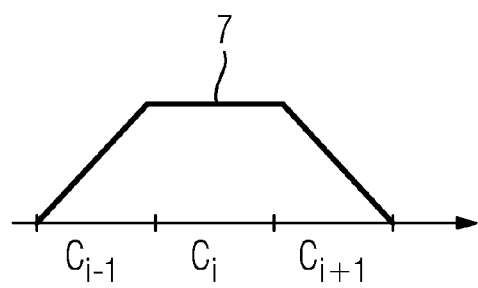
FIG. 3 shows a diagram of a possible weighting of projection images of adjacent time segments.

Three-dimensional reconstruction data records, in the present instance N in number, are now determined by reconstruction respectively from these sets of projection images (in other words N sets) in a step 6, for example using the Feldkamp algorithm. It is conceivable here just to use the projection images $P_{j,i}$, which are also assigned precisely to the cardiac phase, in other words the time segment $C_i$. The data space for avoiding noise and sampling artifacts can however also be extended by a weighting. One example of this is shown in FIG. 3. A weighting function 7 is used there, which allows projection images of adjacent time segments $C_{i-1}$ and $C_{i+1}$ to be included with a lower weighting. The weighting function 7 can of course also be selected in a different form and can be a function of the specifically considered time segment $C_i$, it being necessary to take into account here how significant the deviations can be in adjacent time segments, see for example the profiles 3.

Alternatively however it is also conceivable to use an iterative method for reconstructing the three-dimensional reconstruction image data records, which ultimately takes into account a three-dimensional orientation image data record, which has been reconstructed from all the recorded projection images for all the time segments of the cardiac cycle, it being possible in particular to use the McKinnon-Bates algorithm.

It should also be noted here that the achievement of a better angle sampling was already taken into account when determining the recording parameters in step 2, as for example the recording rate of the radiation detector can be doubled while using the same C-arm rotation speed, provision also being able to be made in this context for reducing the dose per projection image to keep the total dose constant.

Finally in step 6 interpolation-based algorithms for reducing metal artifacts are also used to eliminate artifacts due to catheters present in the heart, in this instance artifacts of a so-called pigtail catheter and the pacing catheter.

High quality three-dimensional reconstruction image data records are thus obtained, which show the movement state of the heart for each of the individual time segments $C_i$.

These can now be combined in a step 7 in the correct temporal sequence within the cardiac cycle, to obtain the four-dimensional angiography data record 8.

Figure 4:
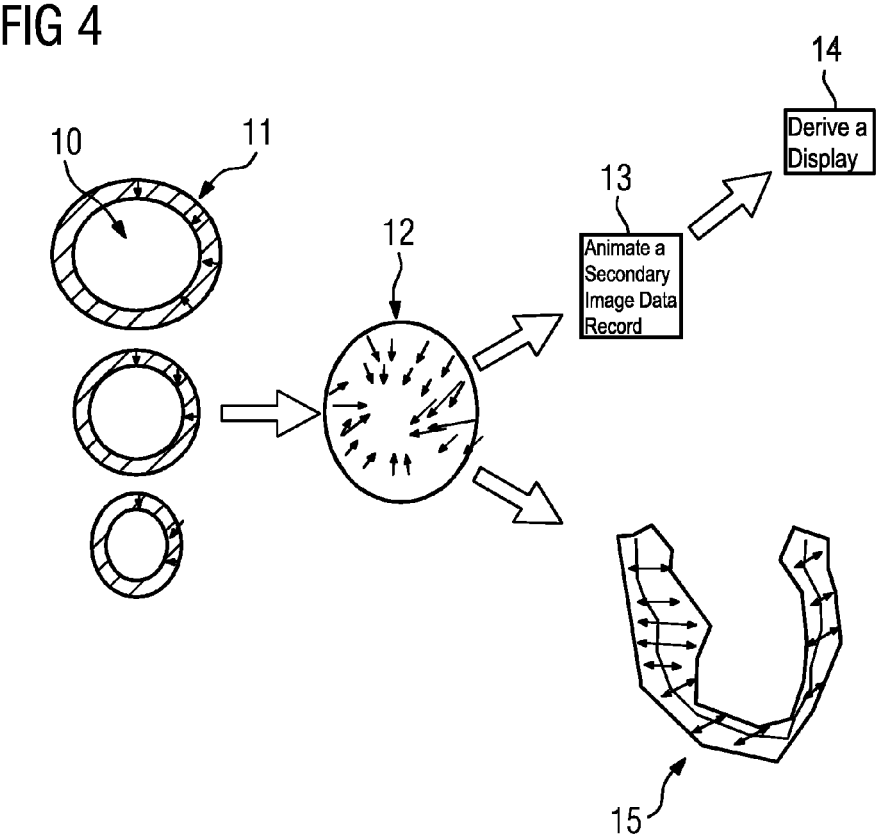
FIG. 4 shows a diagram of the possible evaluation and use of the four-dimensional angiography data record.

This can now be further utilized in different ways in a step 9, as explained in more detail with reference to FIG. 4. Segmentation is first performed there to evaluate the four-dimensional angiography data record 8, with both the lumen 10 of vessels of interest and the heart as well as the wall 11 of the vessels of interest and the heart being segmented for each time segment of the cardiac cycle. As a result it is possible to track how the heart, vessels and walls 11 behave over the period of the cardiac cycle, so a movement model 12 results, for example in the form of a movement vector field, as shown schematically in FIG. 4. In the present instance however the movement model 12 also contains the movements of the walls 11, in particular including their thickness changes over the cardiac cycle. This movement model can be used in two different ways, both of which are shown in FIG. 4. On the one hand it is possible to use the movement model 12 to animate a preoperative secondary image data record, step 13, which takes place after registration. Secondary image data records can be for example secondary image data records recorded before an intervention, in particular a minimally invasive intervention, using a different modality, in this instance a magnetic resonance image data record, which shows the heart region with particularly high resolution but statically. This secondary image data record can now be animated with knowledge of the time point in the cardiac cycle to which it corresponds using the movement information of the movement model 12, so that the movement of the heart and/or vessels can also be made visible in the secondary image data record. This can serve the purpose of a display but in the present instance the dynamization result is used in a step 14 to provide assistance with navigation and guidance during a minimally invasive intervention.

To this end in a step 14 during the minimally invasive intervention two-dimensional fluoroscopy images are recorded continuously, with a display derived from the animated secondary image data record superimposed thereon being displayed according to the cardiac phase currently to be ascertained from an EKG signal, specifically the current time segment. This allows excellent navigation and guidance of minimally invasive instruments, as the anatomy can be displayed with adjusted movement and high resolution in addition to the current fluoroscopy image.

A further use for the movement model 12 is to generate a display, which shows the movement of at least one of the walls 11, in particular the heart wall. Such a display 15 is shown schematically in FIG. 4. Pathologies and infarction tissue that may be present can be derived for example from the movement of the heart wall. The movement of the heart wall and/or other vessel walls can also be displayed for example in the manner of an ultrasound-type display.

FIG. 5 shows a slightly modified exemplary embodiment of the inventive method compared with the first exemplary embodiment, with identical processes/steps being provided with the same reference characters for clarity. The recording parameters determined in step 2, which were determined as a function of the heart stimulation (box 1) for synchronization of the recording operation with the heart movement, are not only used to record projection images with contrast agent and corresponding reconstruction image data records in steps 4-6 but in a step 16 a mask run also takes place, in other words mask projection images are recorded using the same recording parameters with the clearly defined heart rate, without moving the patient compared with recording step 5, said mask projection images then being able to be reconstructed three-dimensionally in a corresponding manner for the same time segments of the cardiac cycle in a step 17 to form mask image data records. The three-dimensional mask image data records are subtracted in a step 18 from the reconstruction image data records from step 6 and the determination of the four-dimensional angiography data record in step 7 then takes place on the basis of the subtraction images determined in step 18. This therefore allows the inventive method also to be performed as a variant of digital subtraction angiography.

FIG. 6 finally shows a basic diagram of an inventive x-ray facility 19. It has a C-arm 20, on which a radiation source 21 and a radiation detector 22 are disposed opposite one another. The C-arm 20 can be rotated about a rotation axis 23 with the recording arrangement, which comprises the radiation source 21 and the radiation detector 22, around a patient 25 (only shown in outline) supported on a patient couch 24 (see arrow 26).

The operation of the x-ray facility 19 here is controlled by a control facility 27, which is configured to perform the inventive method.

To perform the inventive cardiac pacing, in other words the heart stimulation to achieve a stable heart rate, a pacing catheter shown as 28 can be inserted into the patient, which in the present exemplary embodiment is activated by a catheter control device 29, which is connected for communication purposes to the control facility 27. An EKG measuring device 30 (only shown in outline) is also present at the workstation of the x-ray facility 19 and can be used to record the EKG signal of the patient 25 for example during the recording of fluoroscopy images for monitoring a minimally invasive intervention, in order correspondingly to determine a time segment of the cardiac cycle, which shows how an animated secondary image data record is to be superimposed. The EKG measuring device 30 can however also be operated during the recording of the projection images within the context of the present invention.

Although the invention has been illustrated and described in more detail using the preferred exemplary embodiment, the invention is not restricted by the disclosed examples and other variations can be derived therefrom by the person skilled in the art without departing from the scope of protection of the invention.

The invention claimed is:

1. A method for recording a four-dimensional angiography data record using an x-ray facility with a C-arm, comprising:
   recording projection images from different projection directions at different time segments of a cardiac cycle of a patient;
   reconstructing a number of three-dimensional reconstruction image data records assigned respectively with a temporal assignment to a time segment of the cardiac cycle from the projection images; and
   combining the three-dimensional reconstruction image data records to form the four-dimensional angiography data record with the temporal assignment; and
   selecting at least one recording parameter describing the temporal assignment as a function of cardiac stimulation to ensure a stable heart rate during the recording so that the projection images are recorded synchronized with the cardiac cycle.

2. The method as claimed in claim 1, wherein the projection images are recorded during a single rotational movement of the C-arm and/or each projection image for the time segment is recorded in each cardiac cycle, and wherein the recording frequency is selected as a multiple of the heart rate.

3. The method as claimed in claim 1, wherein the heart rate is set at 80 to 130 bpm, and/or 95 to 105 bpm, and/or 30 to 40 bpm, and/or 35 bpm.

4. The method as claimed in claim 1, wherein the projection images are recorded during a fill phase after administration of a contrast agent.

5. The method as claimed in claim 4, wherein a series of two-dimensional images is recorded after administration of a test bolus, and wherein a delay time is determined from the two-dimensional images after administration of a main bolus.

6. The method as claimed in claim 4, wherein a spread of the contrast agent is monitored by a fluoroscopy or 2D digital subtraction angiography before the recording of the projection images and after administration of the contrast agent.

7. The method as claimed in claim 4, wherein mask projection images are recorded at the cardiac stimulation with the selected recording parameter, and wherein three-dimensional mask image data records are determined from the mask projection images for each time segment of the cardiac cycle and are subtracted from the reconstruction image data records to determine the angiography data record.

8. The method as claimed in claim 1, wherein projection images of adjacent time segments of the cardiac cycle have a lower weighting when reconstructing the reconstruction image data records.

9. The method as claimed in claim 1, wherein a three-dimensional orientation image data record is reconstructed from the projection images, and wherein the reconstruction image data records are reconstructed iteratively with the three-dimensional orientation image data record.

10. The method as claimed in claim 1, wherein the reconstruction image data records are corrected in respect of an instrument disposed within the patient by applying a metal artifact reduction algorithm, and wherein the instrument comprises a catheter.

11. The method as claimed in claim 1, wherein at least one vessel and/or organ is segmented in the angiography data record, and wherein a movement model of the segmented vessel and/or organ is derived from the segmentation.

12. The method as claimed in claim 11, wherein the movement model animates a static secondary image data record that shows the vessel and/or organ.

13. The method as claimed in claim 12, wherein the animated static secondary image data record is displayed when monitoring an intervention to be performed on the patient as a function of a recorded electrocardiogram that is superimposed with a current fluoroscopy image.

14. The method as claimed in claim 1, wherein at least one wall of at least one vessel and/or organ is segmented in the angiography data record, wherein the organ comprises hear of the patient, wherein a movement model of the wall including a wall thickness is determined as a function of the time segments in the cardiac cycle and is displayed as a ultrasound-type display.

15. An x-ray facility, comprising:
   a C-arm comprising a radiation source and a radiation detector disposed opposite one another; and
   a control facility configured to perform a method as claimed claim 1.

* * * * *